United States Patent
Messersmith et al.

(10) Patent No.: US 7,208,171 B2
(45) Date of Patent: Apr. 24, 2007

(54) INJECTABLE AND BIOADHESIVE POLYMERIC HYDROGELS AS WELL AS RELATED METHODS OF ENZYMATIC PREPARATION

(75) Inventors: Phillip B. Messersmith, Clarendon Hills, IL (US); Bi-Huang Hu, Chicago, IL (US); Marsha Ritter Jones, Chicago, IL (US)

(73) Assignee: Northwestern University, Evanston, IL (US)

( * ) Notice: Subject to any disclaimer, the term of this patent is extended or adjusted under 35 U.S.C. 154(b) by 344 days.

(21) Appl. No.: 10/699,584

(22) Filed: Oct. 31, 2003

(65) Prior Publication Data

US 2004/0265951 A1 Dec. 30, 2004

Related U.S. Application Data

(60) Provisional application No. 60/422,569, filed on Oct. 31, 2002.

(51) Int. Cl.
*A61F 2/02* (2006.01)
*C12N 9/10* (2006.01)
*A61K 38/02* (2006.01)
*A61K 38/05* (2006.01)

(52) U.S. Cl. ............... 424/422; 623/23.75; 623/23.76; 435/193; 514/2; 514/19

(58) Field of Classification Search ............... 424/422; 623/23.75, 23.76; 435/193; 514/2, 19
See application file for complete search history.

(56) References Cited

U.S. PATENT DOCUMENTS

| | | | | |
|---|---|---|---|---|
| 4,908,404 A | * | 3/1990 | Benedict et al. ......... | 525/54.11 |
| 5,156,956 A | | 10/1992 | Motoki et al. | |
| 5,428,014 A | * | 6/1995 | Labroo et al. ................ | 514/12 |
| 5,490,980 A | * | 2/1996 | Richardson et al. ....... | 424/94.6 |
| 5,525,336 A | | 6/1996 | Green et al. | |
| 5,549,904 A | | 8/1996 | Juergensen et al. | |
| 5,563,047 A | | 10/1996 | Petersen | |
| 5,736,132 A | | 4/1998 | Juergensen et al. | |
| 5,834,232 A | | 11/1998 | Bishop et al. | |
| 5,939,385 A | | 8/1999 | Labroo et al. | |
| 5,968,568 A | | 10/1999 | Kuraishi et al. | |
| 6,010,871 A | * | 1/2000 | Takahara et al. .......... | 435/68.1 |
| 6,129,761 A | | 10/2000 | Hubbell | |
| 6,267,957 B1 | | 7/2001 | Green et al. | |
| 6,322,996 B1 | | 11/2001 | Sato et al. | |
| 6,325,951 B1 | | 12/2001 | Soper et al. | |
| 6,331,422 B1 | | 12/2001 | Hubbell et al. | |
| 2003/0109587 A1 | | 6/2003 | Mori | |

OTHER PUBLICATIONS

Sperinde et al. ("Synthesis and characterization of enzymatically-cross-linked poly(ethylene glycol) hydrogels," Macromolecules 30:5255-5264, 1997.*

Crescenzi et al. New Gelatin-Based Hydrogels via Enzymatic Networking. Published On-Line Oct. 1, 2002. Biomacromolecules 2002, vol. 3, pp. 1384-1391.

Chen et al. Enzymatic Methods for in Situ Cell Entrapment and Cell Release. Published On-line Sep. 30, 2003. Biomacromolecules 2003, vol. 4, pp. 1558-1563.

Fuchsbauer et al. Influence of Gelatin Matrices Cross-linked with Transglutaminase on the Properties of an Enclosed Bioactive Material Using B-galactosidase as Model System. Biomaterials. 1996, vol. 17, No. 40, pp. 23415-23420.

Hohenadl et al. Two Adjacent N-terminal Glutamines of BM-40 (Osteopnectin, SPARC) Act as Amine Acceptor Sites in Transglutaminase c catalyzed Modifications. J Biol Chem. 1995, vol. 270. No. 40, pp. 23415-23420.

* cited by examiner

Primary Examiner—Jon Weber
Assistant Examiner—Rosanne Kosson
(74) Attorney, Agent, or Firm—Quarles & Brady LLP

(57) ABSTRACT

The invention is related to biomimetic gels that are prepared enzymatically, using a transglutaminase to cross-link polymer-peptide conjugates of rational design.

3 Claims, 12 Drawing Sheets

INJECTABLE AND BIOADHESIVE POLYMERIC HYDROGELS AS WELL AS RELATED METHODS OF ENZYMATIC PREPARATION

This application claims priority from the provisional application Ser. No. 60/422,569, filed Oct. 31, 2002, the entirety of which is incorporated herein by reference.

The United States government has certain rights to this invention pursuant to Grant No. DE13030 from the National Institutes of Health to Northwestern University.

BACKGROUND OF THE INVENTION

Polymer hydrogels have structural similarities to numerous macromolecular components in the human body, are generally considered biocompatible, and have been investigated extensively as materials useful for drug delivery, tissue repair and tissue engineering, as well as for use as surgical sealants and adhesives. With increasing frequency, polymer hydrogels are designed for in situ gelation from a liquid precursor, thereby allowing minimally invasive administration via syringe or needle.

Existing hydrogel systems, formed chemically or physically, are subject to several limitations. Chemically cross-linked hydrogels often employ toxic cross-linking agents and/or radicals, and the resulting hydrogels are often non-biodegradable. On the other hand, physical hydrogels—formed through ionic interactions, hydrophobic interactions, hydrogen bonding, or phase transition—are relatively weak and can be prone to unwanted or uncontrollable degradation through ion exchange, ion diffusion, or monomer dissolution. An alternate approach—solidification by enzymatic cross-linking—has two principal advantages, compared to other hydrogel systems. First, an enzyme has substrate specificity to allow controllable gel formation. Second, an enzymatic method can be applied to the in vivo utilization of cross-linked hydrogels, under appropriate physiological conditions.

Transglutaminases (e.g. protein-glutamine:amine γ-glutamyltransferase, EC 2.3.2.13) catalyze a post-translational acyl-transfer reaction between the γ-carboxamide groups of peptide-bound glutamine residues and the ε-amino groups of lysine residues in proteins, or certain primary amino groups, resulting in the cross-linking of proteins through the formation of ε-(γ-glutamyl)lysine isopeptide side-chain bridges. Although several biological fluids are known to undergo rapid transglutaminase (TGase) catalyzed hydrogel formation, previous attempts to use TGase with peptide modified synthetic polymers have resulted in slowly gelling systems. Although proteins are typical TGase substrates, the prior art has demonstrated that synthetic poly (amino acids) and peptide-modified poly(ethylene glycol) can be cross-linked with hydrogel formation. Recently, factor XIII (plasma transglutaminase) was reported to catalyze a hydrogel formation. However, due to the stringent substrate specificity of factor XIII, a 20 amino acid-long peptide from the cross-linking γ-chain of fibrinogen was first, necessarily, synthesized and conjugated to a branched polyethylene glycol (PEG) polymer. The complex preparation of the initial conjugate made a large-scale hydrogel preparation difficult. In both this instance and using synthetic peptides, the time required for gelation was considerably longer than useful for many clinical applications.

SUMMARY OF THE INVENTION

Figure 1:
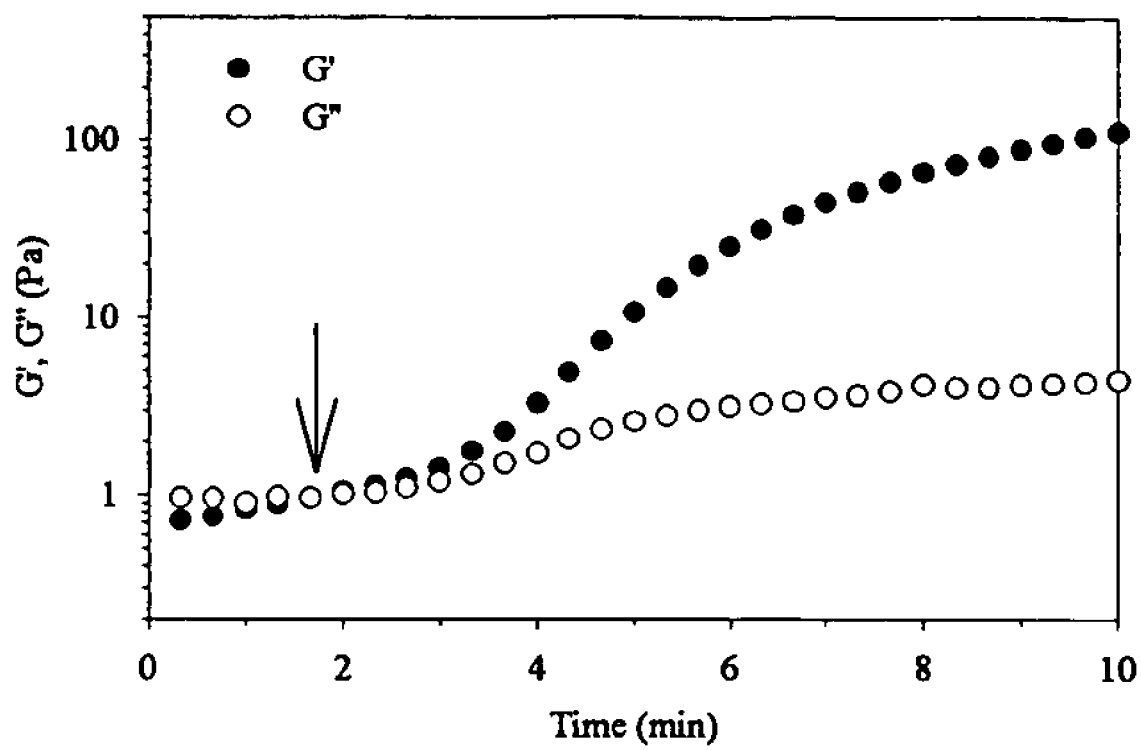
FIG. 1. Oscillatory rheology of a solution containing polymer-peptide conjugates 1, 2 and TGase. The arrow indicates the time at which the gel point was reached.
Figure 2:
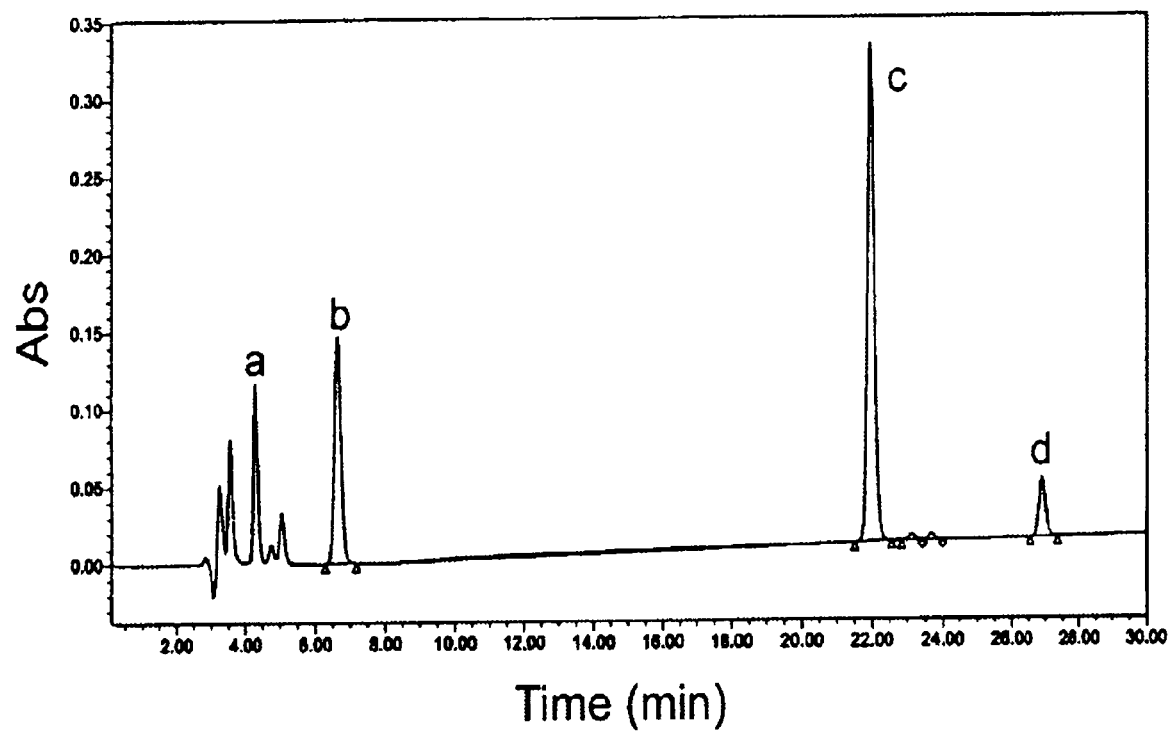
FIG. 2. RP-HPLC analysis of the reaction mixture containing Ac-Phe-Lys-Gly-$NH_2$ (0.1 mM), dns-ε-aca-QQIV (0.5 mM), and guinea pig liver transglutaminase (0.02 U/ml) at 25° C. after 12 min. The peaks were confirmed by LC-ESI/MS (FIG. 3) as Ac-Phe-Lys-Gly-$NH_2$ (a), $^\epsilon$N-dansyl-L-lysine (b), dns-ε-aca-(SEQ ID NO: 1)QQIV (c), and product (d).
Figure 3:
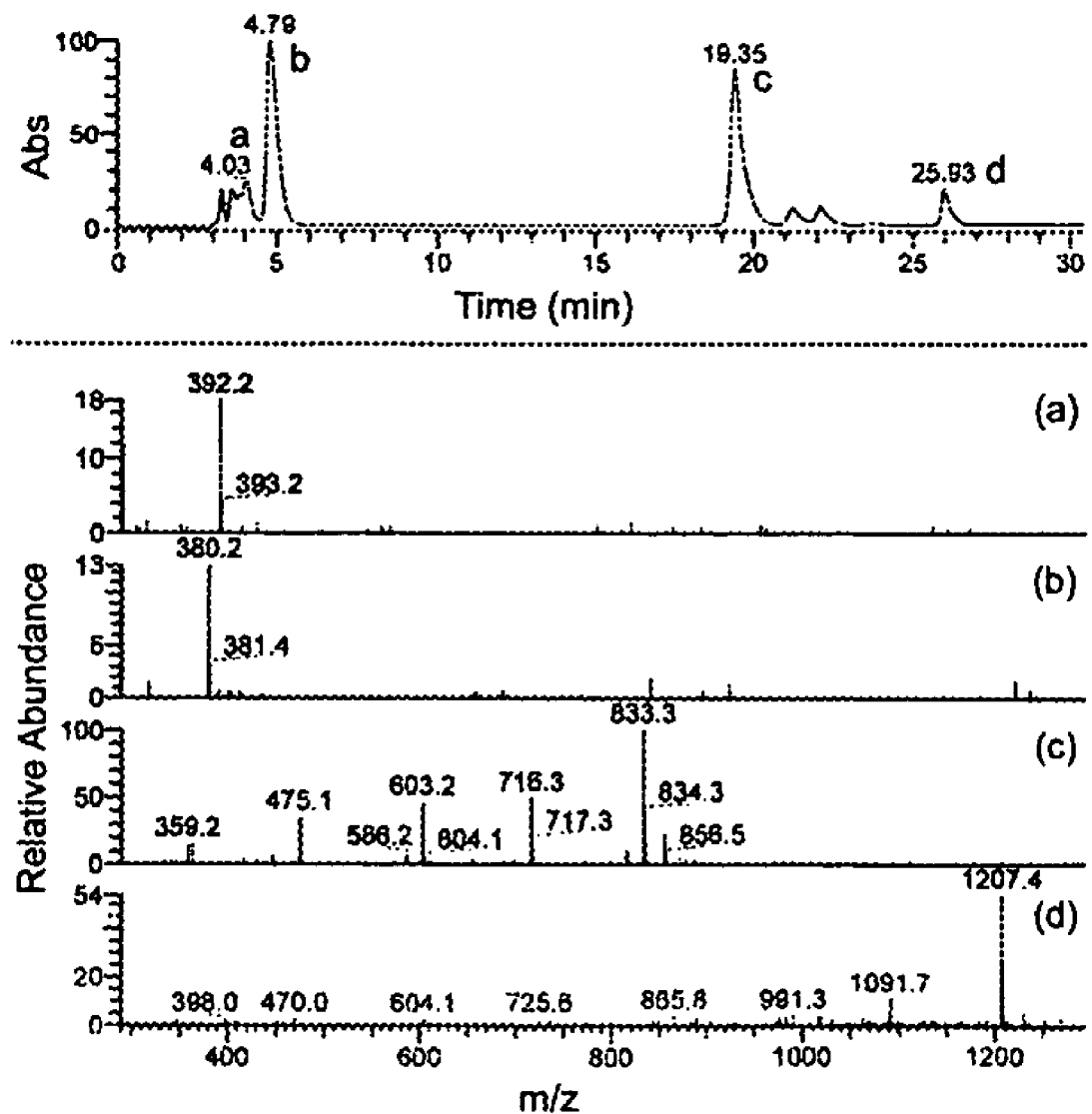
FIG. 3. LC-ESI/MS analysis of the reaction mixture containing Ac-Phe-Lys-Gly-$NH_2$ (2.4 mM), dns-ε-aca-(SEQ ID NO: 1)QQIV (0.5 mM) and guinea pig liver transglutaminase (0.02 U/ml) at 25° C. after 9 min. M/z 392.2 (M+1): Ac-Phe-Lys-Gly-$NH_2$ (a); m/z 380.2 (M+1): $^\epsilon$N-dansyl-lysine (b); m/z 833.3 (M+1): dns-ε-aca-(SEQ ID NO: 1)QQIV (c); and m/z 1207.4 (M+1): the cross-linking product (d).
Figure 4:
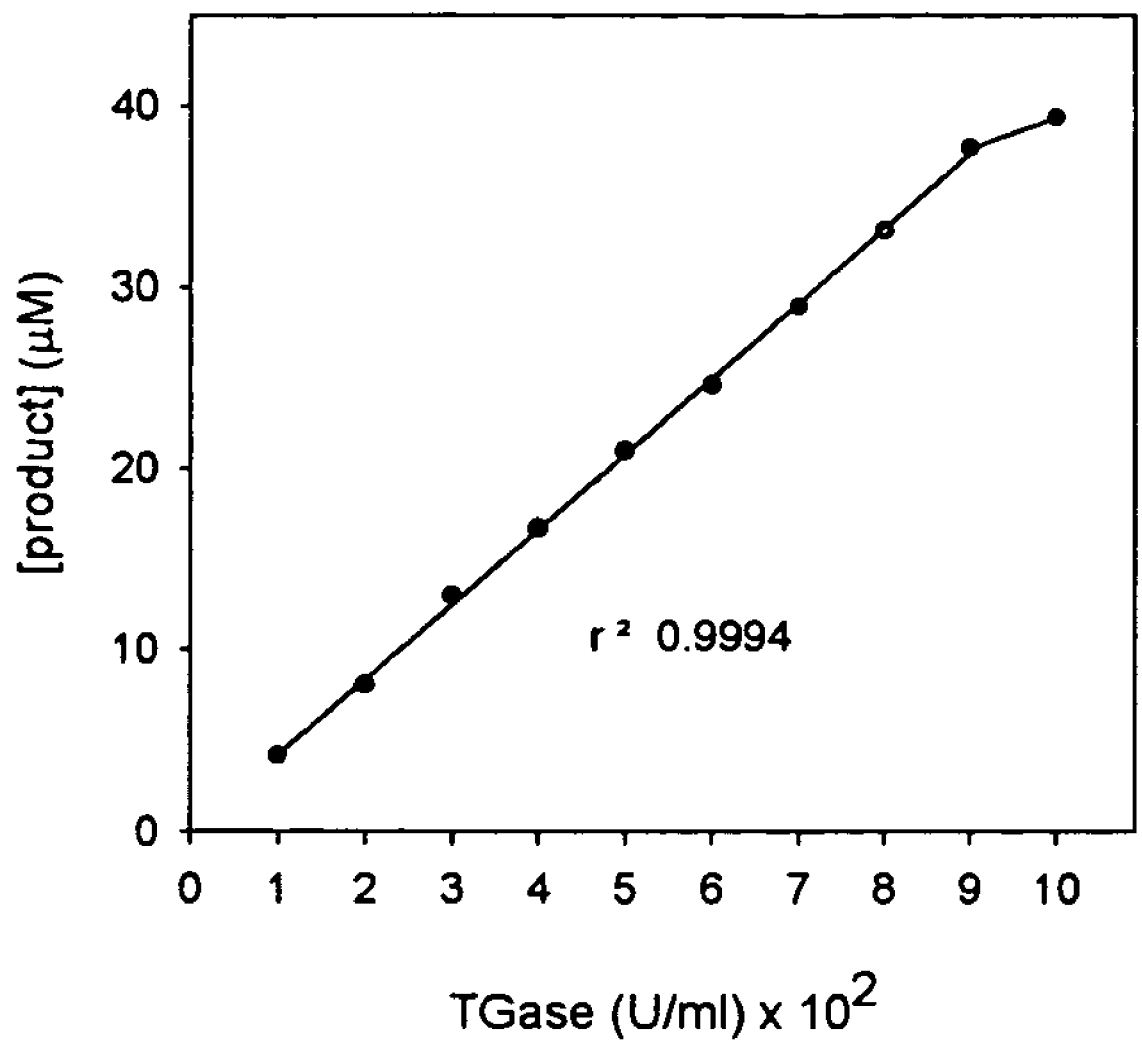
FIG. 4. Product formation at 2 min versus concentration of guinea pig liver transglutaminase for Ac-Phe-Lys-Gly-$NH_2$ (0.1 mM).
Figure 5:
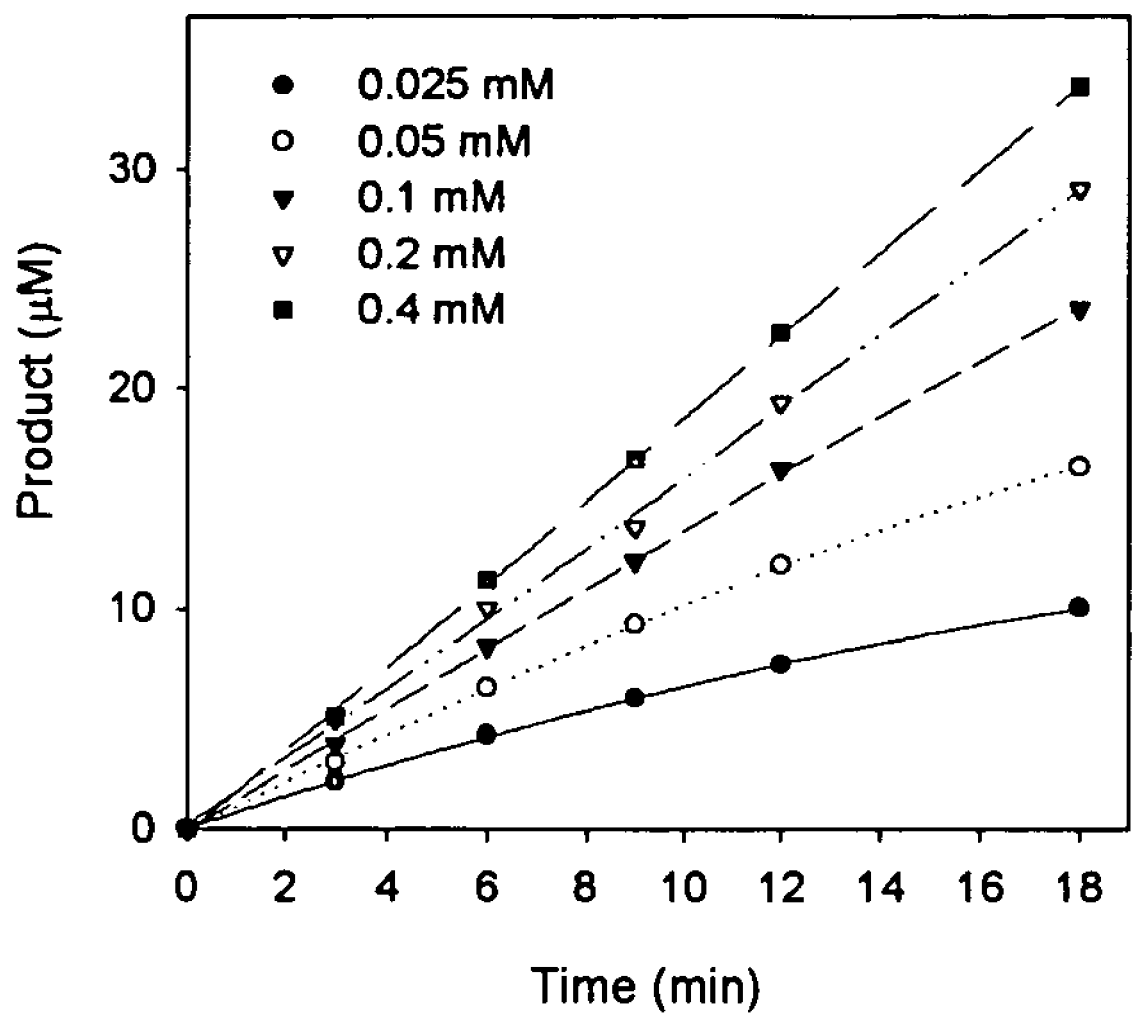
FIG. 5. Time course of the reaction between various concentrations of DOPA-Phe-Lys-Gly-$NH_2$ and dns-ε-aca-(SEQ ID NO: 1) QQIV (0.5 mM) catalyzed by guinea pig liver transglutaminase (0.01 U/ml).

In light of the foregoing, it is an object of the present invention to provide hydrogel systems and/or method(s) for their preparation or formation, thereby overcoming various limitations of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide a range of polymeric components which undergo rapid gelation under physiological conditions.

It is another object of the present invention to identify suitable TGase substrates, short amino acid sequences readily available through known synthetic techniques, having enhanced specificities for TGase activity.

It is another object of the present invention to provide for rational peptide design and conjugation with a range of biocompatible polymeric components, for enzymatic gelation within the minute-timeframe necessary for many medical or political applications.

Other objects, features, benefits and advantages of the present invention will be apparent from this summary and its descriptions of various embodiments, and will be readily apparent to those skilled in the art having knowledge of various polymeric components and enzymatic cross-linking techniques. Such objects, features, benefits and advantages will be apparent from the above as taken into conjunction with the accompanying examples, data, figures and all reasonable inferences to be drawn therefrom.

This invention relates, generally, to a system in which a fluid solution of polymer-peptide conjugates forms covalently cross-linked hydrogels in the presence of an enzyme under physiological or comparable reaction conditions. More specifically, this invention includes the design and preparation of peptide substrates for use in transglutaminase-catalyzed gelation of polymer-peptide conjugates.

In part, the present invention comprises a component system and/or method of using a transglutaminase for polymeric gelation. Such a method comprises (1) providing a first polymeric component coupled to at least one peptide comprising at least one ε-amino moiety; (2) providing a second polymeric component coupled to at least one peptide comprising a γ-carboxamide moiety; or, optionally, providing a polymeric component coupled to at least one peptide comprising at least one ε-amino moiety and at least one peptide comprising at least one γ-carboxamide moiety; and (3) introducing a transglutaminase to the first and second polymeric components, or to a polymeric component comprising both moieties. Generally, such peptides exhibit substrate (e.g., acyl acceptor or acyl donor) specificity with respect to transglutaminase activity, as do the coupled peptide-polymer conjugates. A transglutaminase enzyme is available, as known to those in the art, from a variety of biological, bacterial and/or recombinant sources. A gelation system comprising such polymer and peptide components can be used in conjunction with such a biomimetic method.

As demonstrated herein, illustrated by several of the examples provided below, an ε-amino moiety can be provided with a lysine residue of such a peptide. Alternatively, an amino moiety can be provided by a component chemically or structurally similar to such a lysine residue, providing comparable functional effect and/or substrate specificity with regard to the enzymatic activity utilized in this invention. Likewise, a γ-carboxamide moiety can be provided with a glutaminyl residue of such a peptide. In certain embodiments, such a peptide comprises at least two glutamine or glutamic acid residues, or optionally, two to about thirty glutamine of and/or glutamic acid residues. Alternatively, a carboxamide moiety can be incorporated into such a peptide using a chemically or structurally-similar component providing functional effect or substrate specificity comparable to a reactive glutaminyl residue(s).

The peptides of this invention are rationally designed in consideration of the foregoing. Without limitation, such peptides, alone or as coupled or conjugated with a suitable polymeric component, provide an amino moiety, a lysine residue and/or a functionally-comparable acyl acceptor component at between about the second residue position and about the fourth residue position from the peptide N-terminal. Conversely, other such peptides useful with this invention—again, either alone or as coupled or conjugated with a suitable polymeric component—provide at least two contiguous carboxamide moieties, glutaminyl residues and/or functionally comparable acyl donor components of such a peptide.

A range of polymeric components can be utilized in conjunction with the methods of this invention. Without limitation and for purposes of illustration, alginic acid (or a salt thereof) and/or a poly(ethylene oxide), one of numerous linear or branched compounds commercially available, can be used with good effect, synthetically modified as may be required for coupling to an enzyme specific peptide(s) of this invention. Other polymers or polymeric components, including but not limited to those described herein, synthetically modified as desired, can be used with comparable effect in conjunction with the aforementioned biomimetic peptides. Polymer molecular weights and other such physical or chemical parameters can be varied, limitations on which are imposed only by way of enzyme activity and/or resultant gelation. Accordingly, the present invention can also comprise peptides and polymer-peptide conjugates, their corresponding gels or matrix materials and/or systems of gels/matrices having cellular, chemical or therapeutic agents incorporated therein.

In part, the present invention may also be a method of using a biomimetic peptide for polymer gelation. Such a method includes (1) providing a first polymeric component and coupling thereto at least one acyl acceptor peptide comprising at least one lysine residue; (2) providing a second polymeric component and coupling thereto at least one acyl donor peptide comprising at least two contiguous glutaminyl residues; or optionally, providing a polymeric component coupled both to at least one peptide comprising at least one ε-amino moiety and at least one peptide comprising at least one γ-carboxamide moiety, such a polymeric component providing both acyl donor and acceptor substrates sufficient for transglutaminase activity, and (3) introducing a transglutaminase enzyme to the aforementioned polymeric component(s) in an amount and for a time at least partially sufficient for gelation.

For the first time, this invention provides new peptide substrates for tissue transglutaminase, polymer-peptide conjugates, and bioadhesive hydrogels formed by tissue transglutaminase cross-linking. As mentioned above, the new peptide substrates are rationally designed and synthesized. In designing short peptide substrates of TGase, it was recognized that primary amino acid sequence is a major factor in determining the suitability of a peptide as a TGase substrate, and that not all peptides containing Gln or Lys residues are useful good substrates. In acyl donor substrates, primary peptide/protein sequence near the Gln residue is known to play a role in substrate properties. For instance, short peptides containing Gln repeats, as found in involucrin and other proteins, are known to be excellent acyl donors. Regarding an acyl acceptor, it has been shown in the art that the composition and sequence of the residues adjacent to Lys in peptide and protein substrates can have an effect on the amine specificity.

The substrate specificity of these peptides toward transglutaminase was measured by enzymatic kinetic studies. Peptide substrates with high substrate specificity were coupled to polymer molecules, and the polymer-peptide conjugates were purified. These polymer-peptide conjugates were then cross-linked to rapidly form hydrogels by transglutaminase, as may be achieved through a biomimetic approach under physiological conditions. Such covalently cross-linked hydrogels are injectable, may be formed in-situ, and are biodegradable—and are equal to or better than fibrin glue in adhesion to skin tissue or extracellular matrix protein (collagen) membranes.

For purposes of illustration (Table 1), eight acyl acceptor lysine-peptide substrates and three acyl donor glutaminyl-peptide substrates were rationally designed, in light of the preceding, and synthesized by solid phase peptide synthesis using known literature techniques. As shown in certain embodiments, these peptides may be relatively short (usually about four to about six amino acid residues), such that their preparation can be easily and economically scaled up by standard solution synthetic methods.

TABLE 1

Peptide sequences and their substrate specificity toward tissue TGase.

| Peptide Sequence | | $k_{cat}/K_{m,app}$* |
|---|---|---|
| Ac-KG-NH$_2$ | | 10.6 |
| FKG-NH$_2$ | | 61.6 |
| LKG-NH$_2$ | | 48.4 |
| DOPA-KG-NH$_2$ | | — |
| Ac-FKG-NH$_2$ | | 560 |
| Ac-LKG-NH$_2$ | | 482 |
| DOPA-FKG-NH$_2$ | | 1324 |
| DOPA-LKG-NH$_2$ | | 1179 |
| Ac-GQQQLG-NH$_2$ | SEQ ID NO:2 | 34.1 |
| DOPA- GQQQLG-NH$_2$ | SEQ ID NO:2 | 47.9 |
| NH$_2$-GQLKHLEQQEG-NH$_2$ | SEQ ID NO:3 | 47.3 |

*min$^{-1}$mM$^{-1}$.
For details see Examples, below.

For acyl donor attention was focused on peptides containing two to about 5 contiguous glutaminyl (e.g., Gln residues), whereas for acyl acceptor a variety of residues were placed near or adjacent Lys. The peptides were assayed as TGase substrates by monitoring the rate of cross-linking reaction with a known dansyl labeled substrate. The use of fluorescently labeled compounds and RP-HPLC analysis with the aid of LC-ESI/MS, allowed for identification of products and comparison of the kinetic constants of the candidate peptides. The specificity ($k_{cat}/K_{m,\ app}$) values determined under identical experimental conditions reflect the relative specificity of the enzyme toward the substrates; peptides with higher specificities are better substrates for TGase enzyme, indicating the enzyme-catalyzed cross-linking reaction of that peptide will proceed more rapidly.

Under experimental conditions, the specificities of the Lys peptides varied by several orders of magnitude, whereas the specificities of the Gln peptides varied only modestly (Table 1). The acetylated dipeptide Ac—KG-NH$_2$ had a specificity of 10.6 (min$^{-1}$ mM$^{-1}$) for TGase. Addition of a hydrophobic residue (F or L) to the N-terminus of the dipeptide resulted in an approximately 5-fold increase in specificity, and acetylation of the N-terminus of the F/LKG-NH$_2$ tripeptide further increased the specificity ca. 10-fold.

Incorporation of a DOPA residue directly preceding the Lys residue of the peptide KG-NH$_2$ caused the side-chain primary amine of the Lys to entirely lose its ability to serve as an acyl acceptor. However, addition of an N-terminal DOPA residue to the tripeptides Ac—F/LKG-NH$_2$ resulted in ca. 2.4-fold increases in specificity. Remarkably, the specificities of tetrapeptides DOPA-F/LKG-NH$_2$ were enhanced ca. 100-fold compared to the dipeptide Ac—KG-NH$_2$: representing the first successful incorporation of DOPA into TGase substrate.

More subtle differences were noted in the specificities of the acyl donor peptides, with all three designed Gln peptides exhibiting good substrate properties. It is interesting to note that the specificities of representative short peptides of this invention, Ac-(SEQ ID NO:2)GQQQLG-NH$_2$ and DOPA-(SEQ ID NO:2)GQQQLG-NH$_2$, compared favorably to the specificity of NH$_2$-(SEQ ID NO:3)GQLKHLEQQEG-NH$_2$, a peptide derived from the repeat motif found in the keratinocyte protein involucrin, which is known to be an excellent substrate for TGase.

The acyl donor and acyl acceptor peptides of this invention can be separately conjugated or coupled with, for example, PEG. Solutions of such polymer-peptide conjugates rapidly form hydrogels in the presence of transglutaminase under physiological and/or appropriate reaction or end-use conditions. The hydrogels of this invention are adhesive, for example, comparable to type I collagen and guinea pig skin. For example, based on the results of substrate specificity studies, DOPA-FKG (acyl acceptor) and Ac-(SEQ ID NO:2)GQQQLG (acyl donor) were selected and separately coupled to a PEG to form PEG-peptide conjugates 1 and 2 shown in FIGS. 7–8. The PEG-peptide conjugates were analyzed and purified by RP-HPLC, and their structures confirmed by MALDI TOF-MS analysis.

In the presence of TGase, an aqueous fluid containing equimolar amounts of PEG-peptide conjugates 1 and 2 formed a hydrogel within minutes under physiologic conditions. Rheological studies indicated that the hydrogel formed in less than two minutes, as indicated by the crossover of the storage (G') and loss (G") moduli (FIG. 1). The elastic nature of the cross-linked gel was demonstrated by constant values of G' obtained over several decades of frequency in an oscillatory frequency sweep experiment, and the resulting hydrogel was found to be highly elastic, as indicated by constant values of G' at up to 100% strain during a strain sweep experiment (see examples 8–9).

The conjugated peptides clearly retained their TGase substrate characteristics after coupling to PEG, as evidenced by the rapid gelation time observed. The multifunctionality of the PEG-peptide conjugates result in gel network formation. It should be noted, however, that formulations in which Lys-PEG-Lys was used in place of 1 did not form gels under identical conditions (data not shown), demonstrating that at least under the conditions and acceptor conjugate employed, it may not be sufficient to have Lys residues present in one of the PEG polymers, and thereby emphasizing the benefit of using Lys and Gln peptides with high TGase reactivity.

Although the enzyme concentration necessary for rapid hydrogel formation was considerably higher than for TG-induced cross-linking of free peptide, this may be explained in part by the effect of gel network formation on the mobility of TGase enzyme. During incipient network formation resulting from partial cross-linking of the PEG-peptide conjugates, the solution viscosity rapidly increases while the mobility of the enzyme rapidly decreases. Higher enzyme concentration is therefore necessary to ensure sufficient enzyme available to the cross-linking sites during the later stages of gelation, when enzyme mobility is increasingly restricted. Nevertheless, the gelation time demonstrated here approaches that desired for tissue engineering and surgical adhesive applications, and the presence of DOPA suggests that these new hydrogel materials may prove useful in applications where adhesion to tissues is paramount.

As mentioned above, a range of available transglutaminases catalyze a cross-linking reaction between the γ-carboxamide groups of peptide-bound glutamine residues and the ε-amino groups of lysine residues in proteins. Substrate specificity may be optimized through this invention using, in accordance herewith, short peptides by rational design: typically less than about 20 residues and, in certain embodiments, less than about 10 residues, for easier, quicker and more cost effective peptide synthesis. Optimized peptides can be covalently conjugated to linear or branched polymers such as PEG (e.g., linear PEG, and branched PEG—4-arm, 6-arm or 20-arm), hyper-branched polymers such as dendrimers, or linear polymers with multi-functional groups such as but not limited to chitosan, gelatin, soluble collagens, hyaluronic acid, alginates, and albumins. Solutions of such polymer-peptide conjugates can be mixed with therapeutic agents or cells, which can be injected and triggered to hydrogel and entrap the therapeutics or cells in the presence of tissue or an otherwise suitable transglutaminase under physiological conditions in vivo. Alternatively, solutions of these polymer-peptide conjugates can also be applied onto a recipient surface or an anatomical surface for use as a surgical sealant and/or medical adhesive.

In various embodiments, polymer-peptide conjugates in solution or liquid form can be positioned or injected then triggered to rapidly form hydrogels in the presence of tissue transglutaminase in vivo. Such injectable in-situ formed and cross-linked hydrogels may be useful in sustained drug delivery applications as biodegradable reservoirs, tissue repair and engineering as polymeric scaffolds, gene therapy, soft tissue augmentation and cosmetic tissue augmentation in a minimally invasive manner, and as surgical sealant, medical and dental adhesives, and wound dressings.

As demonstrated below, for purposes of comparison, a Fibrin sealant of the prior art (available under the Tisseel trademark) is currently approved for clinic use as a surgical sealant and medical adhesive. However, it contains human and bovine derived proteins, which pose a risk of contamination with viruses or the prions that cause mad cow disease, or bovine thrombin sensitization. The present hydrogel systems have two primary advantages over fibrin sealant: First, the polymer-peptide conjugates are chemically synthesized, and the enzyme could be prepared by recombinant DNA technology. Second, the hydrogel systems of this invention provide better adhesive qualities to type I collagen.

EXAMPLES OF THE INVENTION

The following non-limiting examples and data illustrate various aspects and features relating to the peptides, conjugates, hydrogel systems and/or methods of the present invention, including the cross-linkage of various polymers with a range of short, easily prepared peptides having enhanced enzymatic specificity, as are available through synthetic techniques and methodologies described herein or as would otherwise be known to those skilled in the art. In comparison with the prior art, the present invention provides results and data which are surprising, unexpected and contrary thereto. While the utility of this invention is illustrated through the use of several polymeric components, peptides and conjugates thereof, it will be understood by those skilled in the art that comparable results are obtainable with various other polymers, peptides and conjugates, as are commensurate with the scope of this invention.

Materials. Unless otherwise provided herein: 4-armed PEG with amine end groups ($M_w$=10 k) was purchased from SunBio PEG Shop. Hydroxyl terminated PEG ($M_w$=4 k) and Sephadex® LH-20 were purchased from Fluka. Rink amide resin (0.6 mmol/g), H-Gly-2-ClTrt resin (0.6 mmol/g), DCC, BOP, HOBt, DIEA, NMP, and protected amino acids were purchased from Advanced ChemTech, KY, USA. Transglutaminase from guinea pig liver, Boc-L-Lys(Boc)-OH, and N-Boc-L-DOPA dicyclohexylammonium salt was purchased from Sigma Chemical Company (St. Louis, Mo.). Acetonitrile was from Burdick and Jackson. TFA was from J. T. Baker. Triethylamine ($Et_3N$), piperidine and water (HPLC grade) monodansyl cadaverine were purchased from Aldrich Chemical Company (Milwaukee, Wis.). Dansyl-ε-aminocaproyl-Gln-Gln-Ile-Val (dns-ε-aca-(SEQ ID NO:1) QQIV) was a gift from Dr. Laszlo Lorand of Northwestern University Medical School and prepared using well-known synthetic techniques.

Example 1

Peptide Synthesis. C-terminal amidated peptides were synthesized manually on a Rink amide resin by the Fmoc solid phase peptide synthesis method. Reagents and solvents for peptide synthesis and protected Fmoc-amino acids were purchased from Advanced ChemTech. Boc-L-DOPA was used for the addition of N-terminal DOPA residue. ESI-MS analysis of peptides was performed on a LCQ LC-MS system (Finnigan, Thermoquest, Calif.). Results are shown in Table 2. Amino acid analysis of peptides was performed at the Protein Research Laboratory, University of Illinois at Chicago. Other peptides useful for TGase activity and in conjunction with the polymer conjugates of this invention (e.g., acyl donor peptides 9–11, Table 1) can be prepared in a similar manner.

TABLE 2

Lysine-containing synthetic peptides studied.

| No. | Sequence | Mw* Calc | Mw* Detd | Rt† |
|---|---|---|---|---|
| 1 | Ac-KG-$NH_2$ | 244.2 | 244.1 | 4.02 |
| 2 | FKG-$NH_2$ | 349.2 | 349.2 | 13.75 |
| 3 | LKG-$NH_2$ | 315.2 | 315.2 | 7.87 |
| 4 | Dopa-KG-$NH_2$ | 381.2 | 381.2 | 5.60 |
| 5 | Ac-FKG-$NH_2$ | 391.2 | 391.2 | 19.73 |
| 6 | Ac-LKG-$NH_2$ | 357.2 | 357.2 | 17.72 |
| 7 | Dopa-FKG-$NH_2$ | 528.3 | 528.3 | 18.26 |
| 8 | Dopa-LKG-$NH_2$ | 494.3 | 494.3 | 16.06 |

*Calc: calculated monoisotopic molecular weight;
Detd: determined molecular weight by ESI-MS;
†Rt: retention time in min.

Example 2

Figure 6:
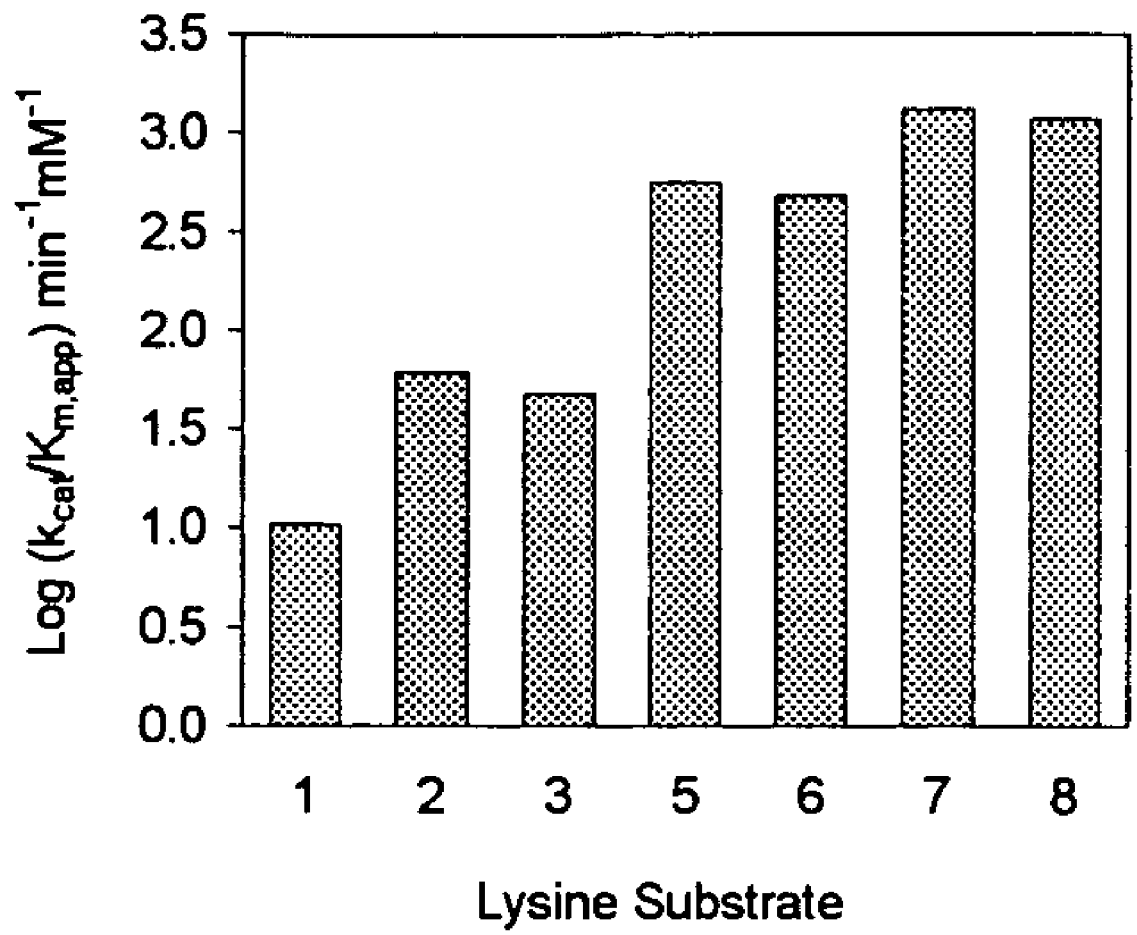
FIG. 6. Comparison of the specificity log ($k_{cat}/K_{m,\ app}$) of liver transglutaminase toward lysine peptide substrates. The bar labels correspond to the numbered peptides of Table 1: Ac-Lys-Gly-$NH_2$ (1), Phe-Lys-Gly-$NH_2$ (2), Leu-Lys-Gly-$NH_2$ (3), Ac-Phe-Lys-Gly-$NH_2$ (5), Ac-Leu-Lys-Gly-$NH_2$ (6), DOPA-Phe-Lys-Gly-$NH_2$ (7), and DOPA-Leu-Lys-Gly-$NH_2$ (8). No cross-linking product was detected with DOPA-Lys-Gly-$NH_2$ (4).

Substrate Specificity. Enzymatic reactions were carried out in 50 mM Tris-HCl buffer containing 5 mM $CaCl_2$, 5 mM DTT, 1 mM EDTA, 0.5 mM dns-ε-aca-(SEQ ID NO:1) QQIV (or 1 mM monodansyl cadaverine for glutamine peptides), varying amounts of a peptide substrate, and purified guinea pig liver transglutaminase (Sigma) (0.01–0.08 U/ml) in a total volume of 200 μl of reaction mixture at pH 8.0, 25° C. At predetermined time intervals, aliquots of the reaction mixture were removed and added to an equal volume of 1% trifluoroacetic acid (TFA) in water or 1% TFA in water containing 0.2 mM ε$N$-dansyl-L-lysine (Sigma) as the internal standard to terminate the reaction. All reaction products were characterized by LC-ESI/MS (Table 3) and quantitatively analyzed by RP-HPLC. Representative results for a few select peptides are shown in FIGS. 2–5. Kinetic constants (Table 4a–b and FIG. 6) were calculated from two methods: fit of the initial rates versus substrate concentrations to the Michaelis-Menten equation using the SigmaPlot® 2000 program with Enzyme Kinetics Module (SPSS Inc., IL); and graphing of the kinetic data using the direct linear plot. A molecular weight of 90,000 Da was used to calculate the enzyme concentration. (See, Folk, J. E.; Cole, P. W. *J. Biol. Chem.* 1966 241, 5518–5525.)

In Table 2 and FIG. 1, the specificity constants ($k_{cat}/K_{m, app}$) indicate that a peptide with a higher constant value is a more specific substrate for TGase enzyme, therefore the enzyme-catalyzed cross-linking reaction with that peptide will be faster.

TABLE 3

Identification of enzymatic reaction products.

| No. | Sequence* | Mw† Calc | Mw† Detd | Rt‡ |
|---|---|---|---|---|
| 1 | Ac-K(Q)G-NH$_2$ | 1059.6 | 1059.3 | 22.34 |
| 2 | FK(Q)G-NH$_2$ | 1164.6 | 1164.6 | 24.42 |
| 3 | LK(Q)G-NH$_2$ | 1130.6 | 1130.5 | 23.28 |
| 4 | Dopa-K(Q)G-NH$_2$ | 1196.6 | n/d | n/d |
| 5 | Ac-FK(Q)G-NH$_2$ | 1206.6 | 1206.4 | 27.50 |
| 6 | Ac-LK(Q)G-NH$_2$ | 1172.6 | 1172.4 | 26.51 |
| 7 | Dopa-FK(Q)G-NH$_2$ | 1343.7 | 1343.4 | 25.14 |
| 8 | Dopa-LK(Q)G-NH$_2$ | 1309.7 | 1309.6 | 24.47 |

*K(Q): □-(□-glutamyl dns-aca-QQIV) Lys;
n/d: no product detected;
†Calc: calculated monoisotopic molecular weight;
Detd: determined molecular weight by LC-ESI/MS;
‡Rt: retention time in min.

TABLE 4a

Kinetic constants of liver transglutaminase toward lysine peptides†.

| No. | Sequence | $K_{m, app}$ (mM) | $V_{max, app}$ (μM/min) | $k_{cat}$ (min$^{-1}$) | $k_{cat}/K_{m, app}$ (min$^{-1}$mM$^{-1}$) |
|---|---|---|---|---|---|
| 1 | Ac-KG-NH$_2$‡ | 0.872 | 1.02 | 9.2 | 10.6 |
| 2 | FKG-NH$_2$ | 0.498 | 1.70 | 30.6 | 61.6 |
| 3 | LKG-NH$_2$ | 0.609 | 1.64 | 29.5 | 48.4 |
| 4 | Dopa-KG-NH$_2$ | n/d | | | — |
| 5 | Ac-FKG-NH$_2$ | 46.9 × 10$^{-3}$ | 1.46 | 26.3 | 560 |
| 6 | Ac-LKG-NH$_2$ | 56.0 × 10$^{-3}$ | 1.50 | 27.0 | 482 |
| 7 | Dopa-FKG-NH$_2$ | 17.0 × 10$^{-3}$ | 1.25 | 22.5 | 1324 |
| 8 | Dopa-LKG-NH$_2$ | 19.5 × 10$^{-3}$ | 1.28 | 23.0 | 1179 | n/d: no product detected.
†guinea pig liver transglutaminase 0.01 U/ml and reaction time 3 min.
‡enzyme 0.02 U/ml and reaction time 18 min.
For DOPA-Lys-Gly-NH$_2$ with concentration 0.05–50 mM, enzyme 0.05 U/ml, and reaction time 30 min, no product was detected.

TABLE 4b

Kinetic constants of the acyl donor peptide (9–11) substrates of Table 1.

| No. | $K_{m, app}$ (mM) | $V_{max, app}$ (mM/min) | $k_{cat}$ (min$^{-1}$) | $k_{cat}/K_{m,app}$ (min$^{-1}$mM$^{-1}$) |
|---|---|---|---|---|
| 9 | 0.119 | 1.8 | 4.0 | 34.1 |
| 10 | 0.367 | 7.8 | 17.6 | 47.9 |
| 11 | 0.593 | 12.5 | 28.1 | 47.3 |

Example 3

Protected Peptide Fragment Synthesis. Based on the results of substrate specificity studies, one lysine peptide sequence, DOPA-Phe-Lys-Gly, and one glutamine peptide sequence, Ac-(SEQ ID NO:2)Gly-Gln-Gln-Gln-Leu-Gly, were chosen and synthesized manually as protected peptide fragments by Fmoc strategy on a H-glycine-2-chlorotrityl resin with the following amino acid side-chain protections: trityl (Gln), Boc (Lys), and Boc (α-NH$_2$ of DOPA). Protected peptide fragments were obtained by treatment of the resin with 1% TFA in dichloromethane (DCM), and the cleaved peptide sequences were confirmed by MALDI TOF-MS analysis.

Example 4

Figure 7:
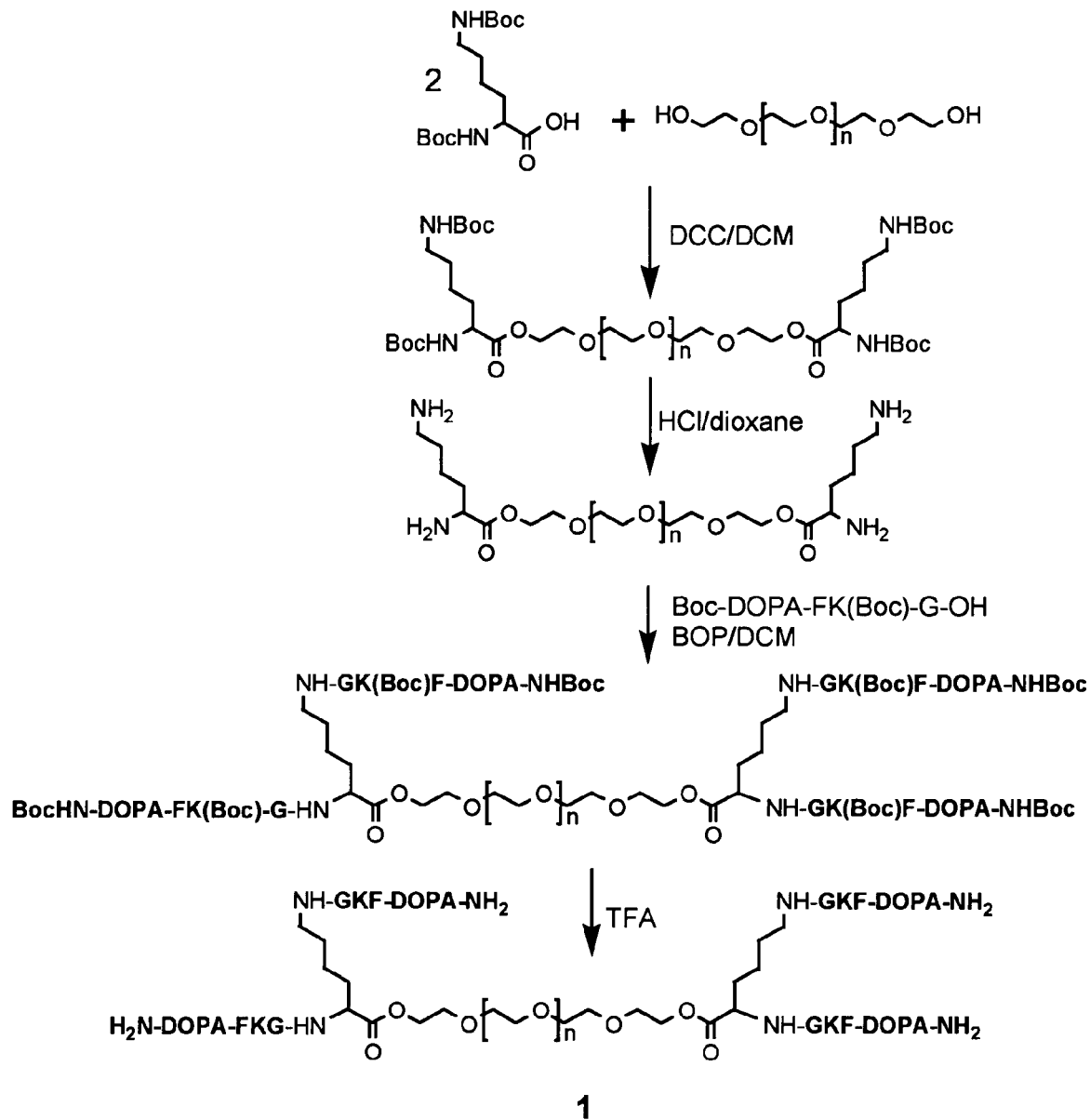
FIG. 7. Synthesis of PEG-lysine peptide conjugate 1.

PEG-Lysine Peptide Conjugate (PEG4KK) Synthesis. The synthetic approach is shown in FIG. 7. 20 g (10 mmol of —OH) PEG diol in 50 ml DCM and 100 ml benzene was azeotropically concentrated under reduced pressure to dry the sample, and the residue was dissolved in 50 ml of DCM. To PEG diol solution, 15 mmol of Boc-L-Lys(Boc)-OH in 50 ml of DCM was added and stirred, followed by addition of 3.1 g (15 mmol) N,N'-dicyclohexylcarbodiimide (DCC) in 20 ml of DCM, and stirred at room temperature overnight. The solution was filtered to remove the solid and concentrated under reduced pressure to afford the product PEG-di-Boc-L-Lys(Boc). Proton NMR confirmed the existence of Boc group in the purified product. PEG-di-Boc-L-Lys(Boc) was then treated with 100 ml of 4 M hydrogen chloride in dioxane at room temperature for 2 hr, and concentrated under reduced pressure. Addition of ether to the residual solution precipitated the product. The product, PEG-di-K, was collected by filtration and dried in vacuum. MALDI TOF-MS confirmed the product structure, and ninhydrin test gave a dark blue color, indicating that the Boc protection group was removed.

A solution of 354 mg (0.48 mmol) Boc-DOPA-Phe-Lys (Boc)-Gly-OH, 400 mg (0.4 mmol) PEG 4000 di-K, 212 mg (0.48 mmol) benzotriazole-1-yl-oxy-tris(dimethylamino) phosphonium hexafluorophosphate (BOP), 74 mg (0.48 mmol) N-hydroxybenzotriazole (HOBt) and 157 μl (0.9 mmol) N,N'-diisopropylethylamine (DIEA) in 3 ml of DCM was stirred for 2 hr at room temperature, followed by addition of cold ether to precipitate the product. The product was collected through centrifugation, dried and treated with TFA-DCM (1:1) at room temperature for 60 min. The solution was dried, and the residue was dissolved in 20 ml of methanol, followed by addition of 20 ml of ether. After storage at −20° C. overnight, the solid was collected by centrifugation and dried in vacuum. The product (1) was further purified by preparative RP-HPLC, and confirmed by MALDI TOF-MS analysis.

Example 5

Figure 8:
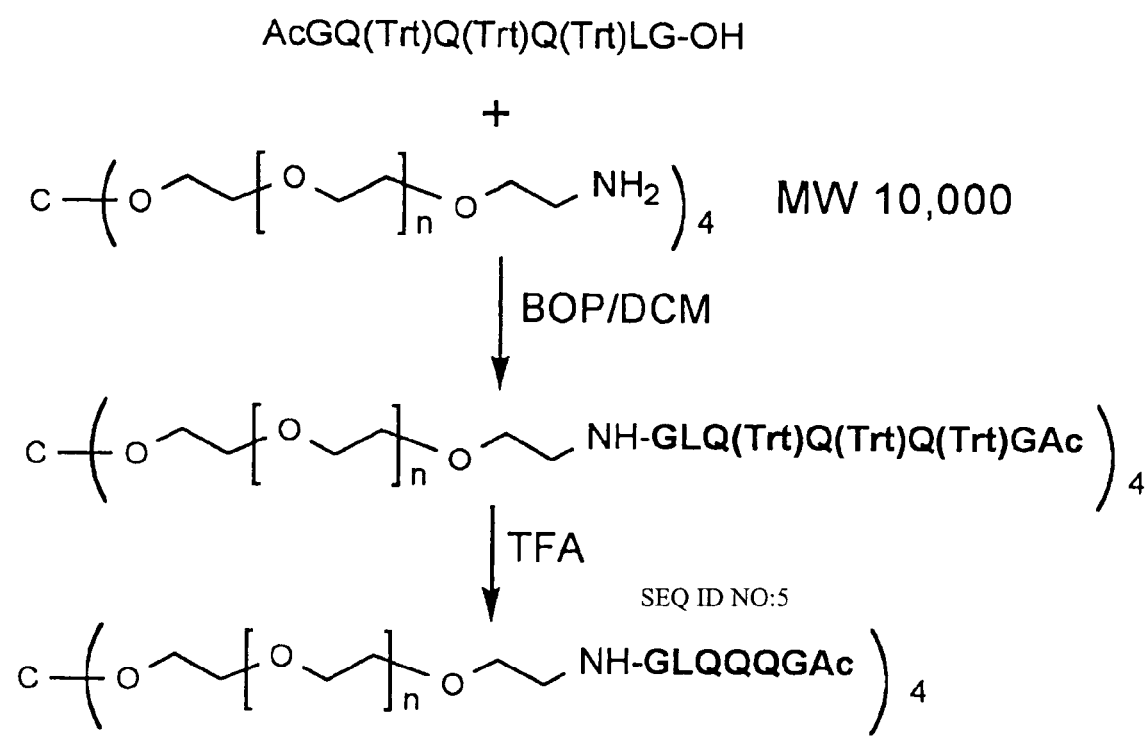
FIG. 8. Synthesis of PEG-glutamine peptide conjugate 2.

PEG-Glutamine Peptide Conjugate (PEG4aQ) Synthesis. The synthetic approach is shown in FIG. 8. A solution of 0.66 g (0.48 mmol) Ac-Gly-Gln(Trt)-Gln(Trt)-Gln(Trt)-Leu-Gly-OH, 0.212 g (0.48 mmol) BOP, 74 mg (0.48 mmol) HOBt, and 250 μl (1.44 mmol) DIEA in 4 ml of DCM was stirred for 10 min at room temperature, followed by addition of 1 g (0.4 mmol of NH$_2$—) 4-armed PEG amine, and stirred overnight. The solution was dried, and the residue was dissolved in 5 ml of MeOH. To the MeOH solution, 45 ml of cold ether was added and stored at −20° C. overnight. The precipitate PEG4aQ(Trt) was collected through centrifugation, dried and further purified by passing through a Sephadex® LH-20 column. PEG4aQ(Trt) was treated with TFA-triisopropylsilane (TIS)-H$_2$O (92:6:2) at room temperature 2 hr. The solution was dried, and the residue was washed with cold ether (50 ml×2), and dissolved in 50 ml of water. The insoluble solid was removed by centrifugation, and the solution was frozen and lyophilized. The lyophilized product (2) was further purified by preparative RP-HPLC, and confirmed by MALDI TOF-MS analysis.

Example 6

Optimization of buffer systems for hydrogel formation. The two peptides, Ac(SEQ ID NO:2)GQQQLG-NH$_2$ and DOPA-FKG-NH$_2$, used to illustrate the polymer-peptide conjugates, above, were chosen as a model system for the optimization of buffer systems for rapid cross-linking: Solution 1. 4 mM Ac(SEQ ID NO:2)GQQQLG-NH$_2$ and 4 mM DOPA-FKG-NH2, 2.67 mM EDTA in water; Solution 2. Buffer containing 20 mM CaCl$_2$; and Solution 3. TGase (0.4 U/ml), 1.33 mM EDTA, and 20 mM DTT in water.

50 µl of solution 2, 25 µl of solution 3, and 25 µl of solution 1 were mixed on ice. After being vortexed, the solution was incubated at 37° C. for 10 min. To the reaction mixture, 100 µl of 0.1 mM dansyl-lysine in 3% TFA aqueous solution was added to stop the reaction. The reactions were run in duplicate. The cross-linked product was quantified by RP-HPLC using dansyl-lysine as the internal standard (see Table 5). Based on these results, further experiments utilized 10 mM CaCl$_2$, 5 mM DTT, and 1 mM EDTA in 100 mM MOPS, pH 7.2 as the gel formation buffer system.

TABLE 5

Comparison of different buffer systems on cross-linked product formation

|  | 100 mM Tris-HCl | 100 mM MOPS pH 7.2 | 200 mM MOPS pH 7.2 | 100 mM HEPES |
|---|---|---|---|---|
| A* | 0.6088 | 0.7411 | 0.7323 | 0.6555 |

A*: Average of (Area of Product)/(Area of dansyl-lysine); buffer concentrations are the final concentrations.

Example 7

Hydrogel Formation. Three solutions were prepared as follows: Solution 1. 4 mM PEG4aQ and 10 mM CaCl$_2$ in 75 mM Tris-HCl, pH 8.0, 1.33 mM EDTA; Solution 2. 8 mM PEG4KK in water; and Solution 3. Transglutaminase from guinea pig liver (16 U/ml) in 50 mM Tris-HCl, pH 8.0, 20 mM DTT, 1.33 mM EDTA. All solutions were cooled on ice for 10 min, after which 25 µl of solution 2, 25 µl of solution 3, and 50 µl of solution 1 were mixed on ice. After being vortexed, the solution was incubated at 37° C. for 10 min. The final reaction solution consisted of 2 mM PEG4aQ and 2 mM PEG4KK in 50 mM Tris-HCl, pH 8.0 (25° C.), 5 mM CaCl$_2$, 5 mM DTT, 1 mM EDTA. A gelation time of less than 2 minutes was observed, as further indicated in FIG. 1, by the cross-over of storage (G') and loss (G") moduli. Alternatively, bacterial TGase, recombinant and otherwise, can be used in conjunction with the gelation of this example and the cross-linking reactions described elsewhere herein. See, for instance, "Enzymatic Methods for in Situ Cell Entrapment and Cell Release," Tianhong Chen, David A. Small, Martin K. McDermott, William E. Bentley, and Gregory F. Payne, Biomacromolecules (published on the web, 30 Sep. 2003).

Example 8

Figure 9A:
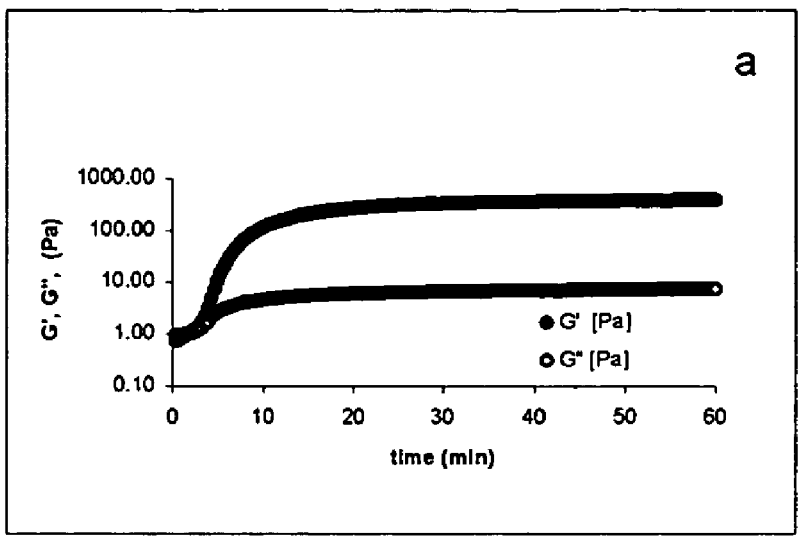
FIG. 9. A. Oscillatory rheology of hydrogel containing 4 mM PEG4aQ and 4 mM PEG4KK in 100 mM MOPS, pH 7.2, 10 mM $CaCl_2$, 5 mM DTT, 1 mM EDTA, and 4 U/ml tissue transglutaminase. a. storage modulus versus time during crosslinking; B. Frequency sweep at 1% strain after 60 minutes crosslinking at 37° C.; C. Strain sweep at 1 Hz frequency after frequency sweep experiment. G'=storage modulus; G"=loss modulus.
Figure 9B:
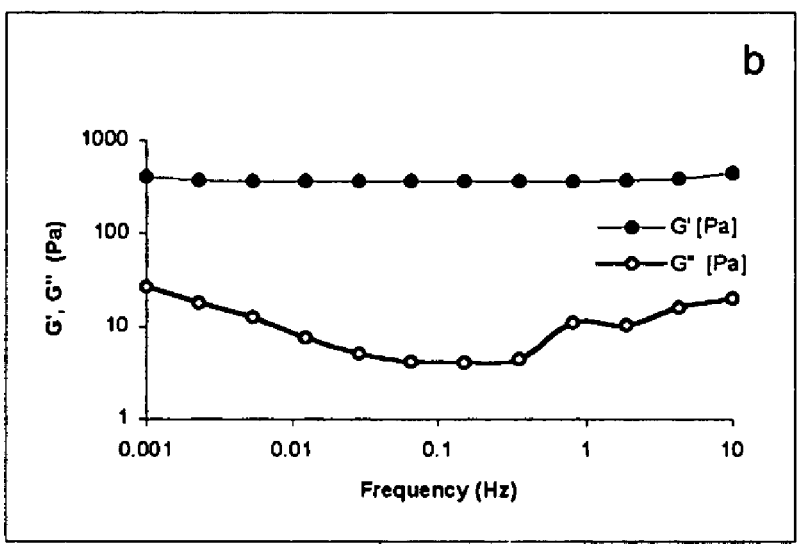
Figure 9C:
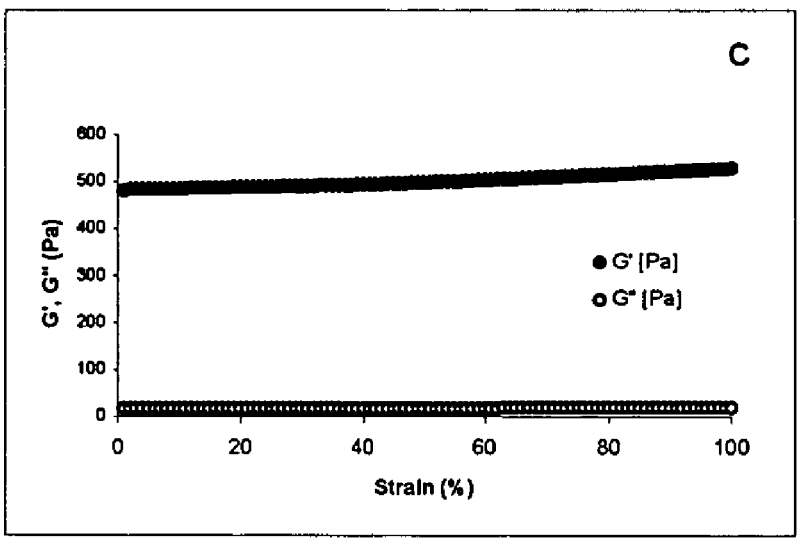

Oscillatory Rheology. Oscillatory rheological experiments were performed with a Paar Physica MCR300 Rheometer with a Peltier device to control temperature using a stainless steel parallel plate (25 mm in diameter). Three solutions were prepared on ice as follows: Solution 1. 8 mM PEG4aQ and 20 mM CaCl$_2$ in 200 mM MOPS, pH 7.20; Solution 2. 16 mM PEG4KK and 2 mM EDTA in water; and Solution 3. 20 mM DTT and 2 mM EDTA in water. 125 µl each of solution 2 and solution 3, and 250 µl of solution 1 were added into a vial containing 2 U of tissue transglutaminase from guinea pig liver and mixed on ice. After vortexing, 400 µl of the solution (4 mM PEG4aQ and 4 mM PEG4KK in 100 mM MOPS, pH 7.2, 10 mM CaCl$_2$, 5 mM DTT, 1 mM EDTA, and 4 U/ml tissue transglutaminase) was loaded onto the thermostated rheometer plate (37° C.), and the top parallel plate (25 mm in diameter) was positioned to hold the solution in a 0.8 mm gap between the two plates. After mineral oil was applied to the edge of the parallel plate for evaporation control, data were collected every 20 s over 60 min. The measurements of the storage and loss modulus were taken at 37° C. in the oscillatory mode at 1 Hz frequency and 1% strain during crosslinking (FIG. 9A). After the gelation experiment, a frequency sweep experiment was performed from 0.001 Hz to 10 Hz with 12 data points at 1% strain (FIG. 9B). Finally, a strain sweep experiment was performed with strain from 1% to 100% at 1 Hz frequency (FIG. 9C).

Example 9

Determination of hydrogel bioadhesion. Bioadhesion properties were measured with solns. 1–3, prepared and mixed as provided herein: Solution 1. 8 mM PEG4aQ3 and 20 mM CaCl2 in 200 mM MOPS, pH 7.20; Solution 2. 16 mM PEG4KK and 2 mM EDTA in water; and Solution 3. 20 mM DTT and 2 mM EDTA in water.

Pieces of full thickness dorsal skin of guinea pig, or bovine collagen type I membrane were glued to the flat surfaces of 2×2 cm test aluminum fixtures using cyanoacrylate glue. The skin or membrane was hydrated in 10 mM phosphate pH 7.4-buffered isotonic saline for 60 min. Just before applying adhesive solution, excess buffer was removed using a Kimwipes® wiper.

Figure 10:
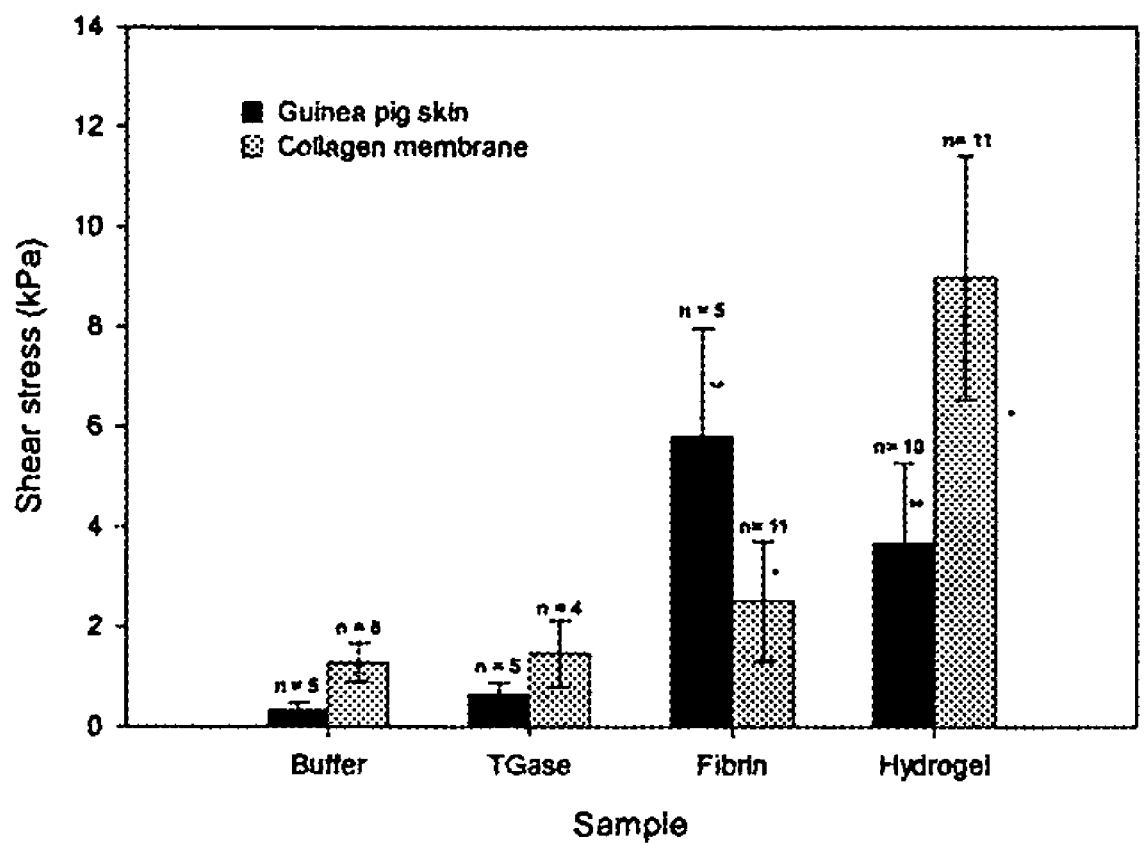
FIG. 10. Shear stress of hydrogel on guinea pig skin and collagen membrane (*P<0.01, **P>0.05).

125 µl of solution 2, 125 µl of solution 3 were added to a vial containing 2 U of tissue transglutaminase from guinea pig liver and mixed on ice, followed by addition of 250 µl of solution 1, and vortexed. 40 µl of the solution was applied onto each hydrated surface, and the surfaces were pressed together using a constant force. The entire assembly was incubated at 37° C. for 2 hr under 100% humidity. The assembly was then mounted in an Instron machine and tested using ASTM D1002 method. Controls were performed in which the formulation described above was replaced with buffer only, enzyme only, and a commercial fibrin sealant purchased from Baxter Healthcare Corp. For the fibrin sealant test, 40 µl of the fibrinogen solution was applied onto one surface and 40 µl of the thrombin solution was applied onto a second surface, and the second surface was pressed onto the first surface. Results obtained are provided in FIG. 10.

Example 10

The following peptide syntheses and enzyme isolation procedures were used in conjunction with the embodiments of examples 11–13, but can be applied more generally with respect to various other embodiments of this invention, including but not limited to the acyl acceptor and donor peptide substrates, polymer conjugates and cross-linked gels of the preceding examples.

Peptide synthesis. Each of the following tissue transglutaminase (tTG) peptide substrates was synthesized manually using fluorenylmethoxycarbonyl (Fmoc) solid phase synthesis. The lysine substrate, phenylalanine-phenylalanine-lysine-glycine-cysteine-$NH_2$ (SEQ ID NO:4)FFKGC-$NH_2$), was synthesized using Rink amide resin. It was cleaved from the resin and deprotected using trifluoroacetic acid (TFA), ethanedithiol (EDT), water, and triisopropylsilane (95:2.5:2.5:1). These reagents were removed via rotor evaporation and the peptide was precipitated in ethyl ether. Once the ethyl ether had evaporated, the peptide was dissolved in 2% acetic acid, frozen at −20° C. and lyophilized. The peptide was stored at −20° C. until use. The yield exceeded 90%, with >85% purity (data not shown). The structure was confirmed with matrix assisted laser desorption ionization time of flight mass spectrophotometry (MALDI TOF) and purity was determined using HPLC.

The glutamine peptide substrate, acetyl-glycine-glutamine-glutamine-glutamine-leucine-glycine (Ac(SEQ ID NO:2)GQQQLG), was synthesized on chlorotrityl resin which facilitated easy cleavage of the protected peptide, AcG(Q(Trtl))$_3$LG (Trtl=Trityl). The peptide was cleaved with 1% (v/v) TFA in dichloromethane (DCM) and precipitated with water (>90% yield). The peptide was dried and stored over phosphorus pentoxide without further purification. The predicted molecular weight of the peptide was confirmed by MALDI TOF MS and purity determined with HPLC.

Isolation of guinea pig tissue transglutaminase. Guinea pig livers (Harlan, Indianapolis, Ind.) were homogenized in 0.25 M sucrose. The homogenate was then centrifuged at 30000 rpm for 1 hour. The supernatant was made 0.01 M sodium acetate, the pH was adjusted to 5 with acetic acid and the solution was centrifuged at 15000 g for 25 minutes. The precipitate was then homogenized with 0.05 M phosphate buffer at pH 6.5. The solution was centrifuged at 15000 g for 35 minutes and applied to a 2.5 cm×12 cm column of DEAE-cellulose that had been equilibrated with 5 mM Tris (pH 7.5). The transglutaminase was eluted with a linear gradient from 0 to 0.7 M NaCl and fractions were collected in 4 mL portions. The fractions that had an absorbance ratio of 260/280 less than 1 were pooled for further purification. A freshly prepared 1% (w/v) protamine sulfate solution was added to the pooled fractions in a ratio of 1:10. The solution was centrifuged at 15000 g for 15 minutes. The precipitate was then homogenized with 0.05 M ammonium sulfate and the solution was centrifuged at 15000 g for 5 minutes. The homogenization and centrifugation of the precipitate formed in the protamine solution was repeated 2 additional times. The supernatant was pooled and dialyzed in 0.5 M NaCl and 5 mM Tris (pH 7.5) overnight. The solution was then frozen at −20° C. and lyophilized. The enzyme activity was analyzed as described in the literature and stored at −20° C. until use. (See, Folk, J., *Methods in Enzymology*, 1970, 17, 889–94.) Unless otherwise noted, the isolation was conducted at 4° C.

Example 11

Figure 11:
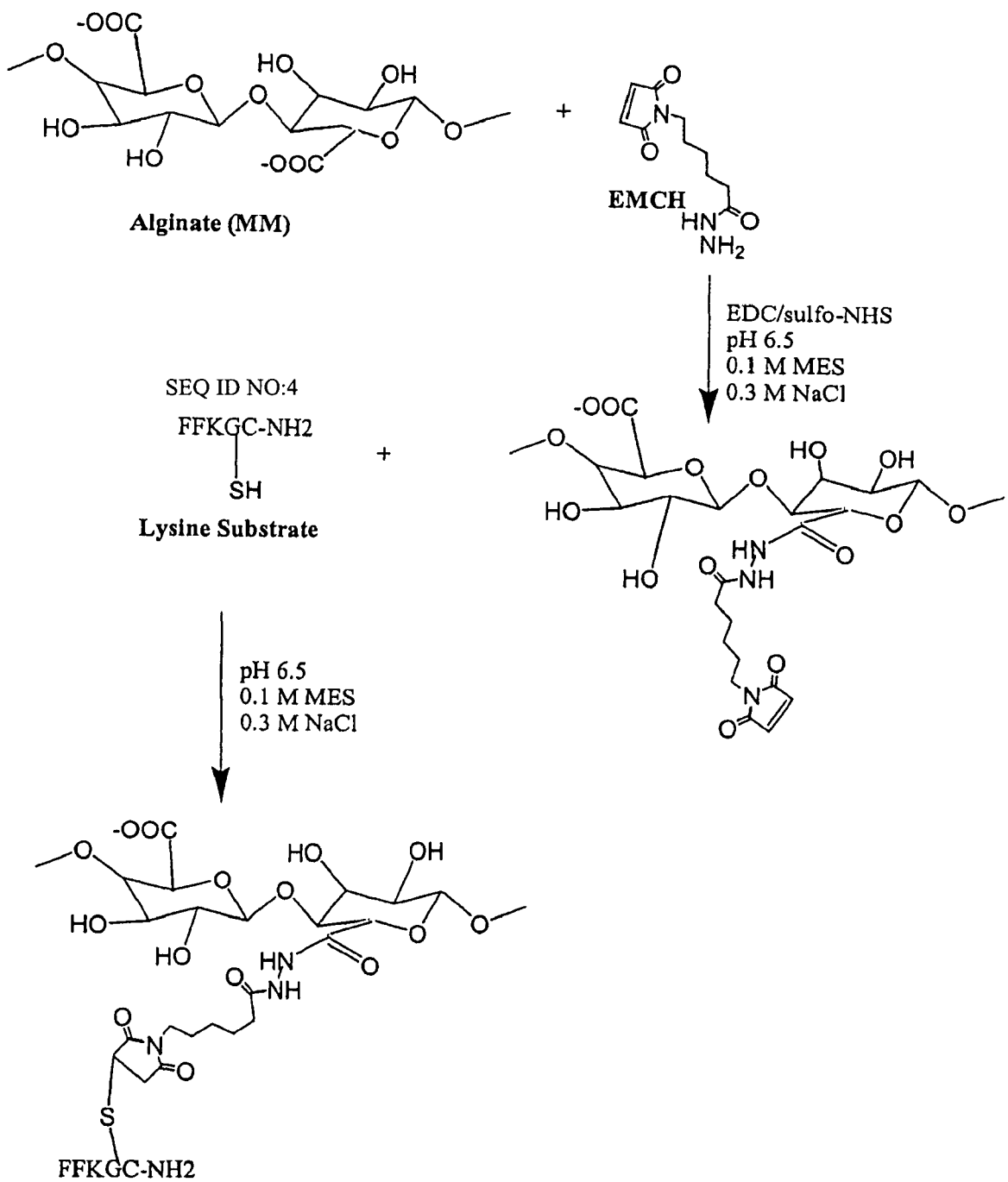
FIG. 11. Synthesis of alginate-lysine peptide conjugate.
Figure 12:
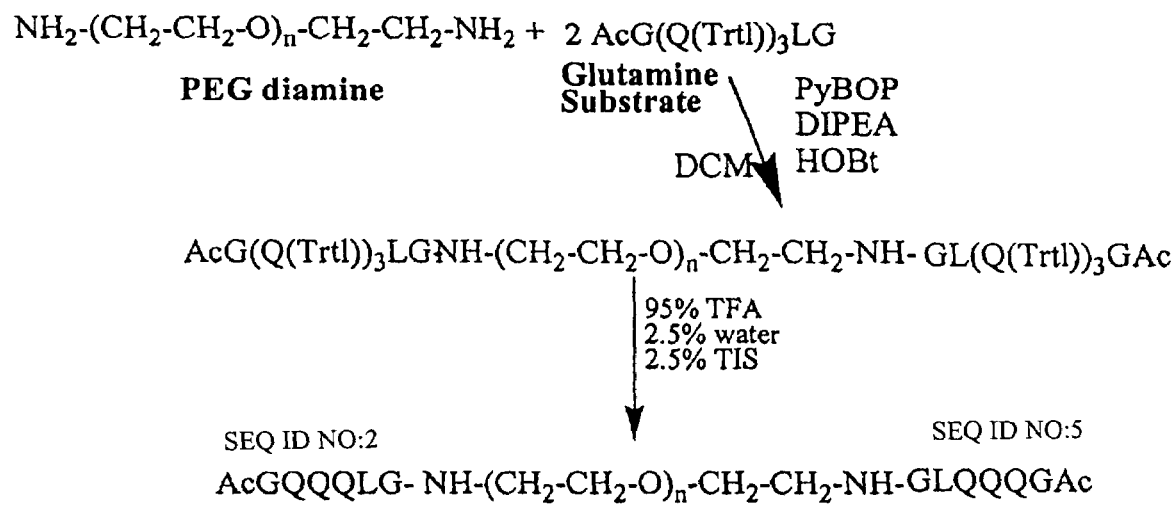
FIG. 12. Synthesis of PEG-glutamine peptide conjugate.

Synthesis of alginate modified with a lysine substrate. A 2% solution of high-mannuronic acid alginate in 0.1 M MES and 0.3 M NaCl at pH 6.5 was combined with 1-ethyl-3-[3-dimethylaminopropyl]carbodiimide hydrochloride (EDC), N-hydroxysulfosuccinimide(Sulfo-NHS) and [N-ε-maleimidocaproic acid] hydrazide (EMCH). The COOH:EDC:sulfo-NHS:EMCH ratio was 8:2:1:2. With reference to FIG. 11, the reaction was performed at room temperature for 2 hours after which the un-reacted solutes and byproducts were removed using centrifugal ultrafiltration for 2.5 hours. The lysine substrate, SEQ ID NO:4 FFKGC-$NH_2$, was then added at equimolar quantity to EDC and the reaction proceeded at room temperature for 3.5 hours. The un-reacted peptide was removed by centrifugal ultrafiltration and solvent exchanged to water. The solution was considered pure when the filtrate tested negative for primary amines utilizing the ninhydrin test. The solution was then lyophilized and stored at −20° C. until use.

The amount of peptide coupled to the alginate was determined using a modified method of the aqueous ninhydrin test. Briefly, 4 mg of the modified alginate was dissolved in 1 M sodium acetate buffer at pH 5. Aqueous ninhydrin reagent (Sigma) was added to the solution in a 0.5:1 ratio. This mixture was heated at 110° C. for 15 minutes after which 15 mL of 50% ethanol was added. The solution was then placed in the dark for an hour followed by the measurement of the absorbance at 570 nm. A standard curve was generated using lysine. Twelve percent (S.D. 2%) of the carboxylic acid groups on alginate were modified with the lysine peptide substrate, a reaction efficiency of about 40%. Final yield of modified alginate was 60–70%.

Example 12

Synthesis of the polyethylene glycol (PEG) modified with the glutamine substrates. The protected glutamine substrate, AcG(Q(Trtl))$_3$LG, benzotriazol-1-yl-oxy-tris (dimethylamino) phosphonium hexafluorophosphate (BOP), 1-hydroxybenzotriazole (HOBt), N,N,-diisopropylethylamine (DIPEA) were combined in a vial and dissolved in DCM in a ratio of 1:1:1:2. The PEG-diamine (MW 3400) was added to the peptide at a ratio of 1:3 and the reaction was conducted at room temperature for 3 hours. TLC was employed to monitor the completion of the reaction. The peptide was then deprotected using TFA:TIS:$H_2O$ (95:2.5:2.5). Methanol was added so that the modified PEG had a concentration of 2% (w/v) of theoretical yield. This solution was then stored at −20 ° C. for 24 hours. The precipitated product was collected by centrifugation, and dissolved in water. The solution was then lyophilized and stored at −20° C. until use. Analysis of the peptide (>90% yield) was performed via MALDI TOF mass spectrometry.

Example 13

Crosslinking of the modified alginate and PEG via transglutaminase. Liposomes, composed of 9:1 1,2 dipalmitoyl-SN-glycero-3-phosphatidylcholine (DPPC) to 1,2 dimystiroyl-SN-glycero-3-phophatidylcholine (DMPC), were used as the vehicle for calcium delivery. This ratio of DPPC:DMPC yields liposomes that release their contents at 37° C. The liposomes were prepared, using a 0.22 M solution of $CaCl_2$, as described in the literature. (See, Westhaus, E., Messersmith, P., *Biomaterials,* 2001, 22, 453–462.) The gel solution consisted of 1.7% (m/v) modified alginate, 1.7% (m/v) modified PEG, tTG at 0 or 8.3 units/mL, 4.5 or 9mM $CaCl_2$, 0.22 M NaCl, and 42 mM Tris. Oscillatory rheometry with a cone and plate configuration was used to determine gelation. (See example 14, below.) The cone angle was 1° while the diameter was 50 mm. The strain was 1% and the amplitude was 0.1 Hz. The solution was placed on the plate at 25° C. Measurements were taken at 25° C. for 3 minutes followed by a linear increase over 12 minutes to 37° C. Finally, the temperature was held at 37° C. for 15 minutes.

Example 14

Oscillatory rheology. Rheological experiments (as described above, but results not shown) on the cross-linked conjugates of example 12 indicate that gelation occurs upon the release of $Ca^{2+}$ from the liposomes. There appears to be a premature release of the liposome content. Preliminary results suggest that this is primarily caused by the modified alginate, transglutaminase, and liposomes interacting (data not shown). Despite this, gelation occurred in all samples containing transglutaminase. The storage modulus of the gels containing transglutaminase was greater than those without it, indicating that transglutaminase was participating in the gelation process. Even at the higher concentrations of $Ca^{2+}$ (9 mM vs. 4.5 mM), where alginate ionic gelation is more significant, the transglutaminase-containing gel still has a superior storage modulus. There is little increase in storage modulus of the gels with an increase in $Ca^{2+}$, perhaps due to alginate sequestering the calcium and minimizing enzymes utilization. In addition, the formation of the gel may prohibit the enzyme mobility to continue crosslinking available peptides.

While the principles of this invention have been described in connection with specific embodiments, it should be understood clearly that these descriptions are added only by way of example and are not intended to limit, in any way, the scope of this invention. For instance, using the synthetic techniques described herein, any one of the aforementioned polymeric components can be conjugated with any one of the aforementioned peptides, with known chemistry and coupling reagents, to provide a range of acyl donor and acyl acceptor polymer-peptide conjugate compounds, for subsequent enzyme-catalyzed, cross-linked gelation. Without limitation, 4-, 6- or 20-armed PEG components and various dendrimeric polymers can be conjugated, in turn, with both acyl donor and acyl acceptor peptides of the sort described in Table 1 and cross-linked, without introduction of another polymeric component. Likewise, one or more alginates can be conjugated with one of or both an acyl donor and acyl acceptor peptide, as described above. The peptide substrates of this invention are limited only with regard to the design principles and considerations provided herein. Conjugation thereof can be extended to the range of polymeric components, suitable for a particular end-use application, using known synthetic techniques provided herein or straightforward modifications thereof, as may be useful for a particular polymer-peptide conjugate, such techniques as could be ascertained by one skilled in the art without undue experimentation.

We claim:

1. A biomimetic gelation system comprising:
   a) a first polymeric component conjugated to at least one acyl donor peptide, wherein the at least one donor peptide comprises at least two contiguous glutaminyl residues;
   b) a second polymeric component conjugated to at least one acyl acceptor peptide, wherein the at least one acceptor peptide comprises a lysine residue; and
   c) a transglutaminase; wherein at least one of said first and second polymeric components comprises poly(ethylene glycol).

2. The new system of claim 1 wherein each of said first and second polymeric componets is conjugated to a plurality of said peptides.

3. The system of claim 1 wherein said first and second polymeric componets are selected from poly(ethylene glycol), chitosan, collagens, hyaluronic acid, alginic acid, albumins and salts of said acids.

* * * * *

UNITED STATES PATENT AND TRADEMARK OFFICE
CERTIFICATE OF CORRECTION

PATENT NO. : 7,208,171 B2  
APPLICATION NO. : 10/699584  
DATED : April 24, 2007  
INVENTOR(S) : Phillip B. Messersmith, Bi-Huang Hu and Marsha Ritter Jones It is certified that error appears in the above-identified patent and that said Letters Patent is hereby corrected as shown below:

Col. 13, Line 31, "chiorotrityl" should be --chlorotrityl--.

Col. 13, Line 34, "dichioromethane" should be --dichloromethane--.

Col. 18, Line 23, [Claim 2], "componets" should be --components--.

Col. 18, Line 27, [Claim 3], "componets" should be --components--.

Signed and Sealed this

Twentieth Day of November, 2007

JON W. DUDAS  
*Director of the United States Patent and Trademark Office*

SEQUENCE LISTING

```
<160> NUMBER OF SEQ ID NOS: 5

<210> SEQ ID NO 1
<211> LENGTH: 4
<212> TYPE: PRT
<213> ORGANISM: Homo sapiens

<400> SEQUENCE: 1

Gln Gln Ile Val
1

<210> SEQ ID NO 2
<211> LENGTH: 6
<212> TYPE: PRT
<213> ORGANISM: Homo sapiens

<400> SEQUENCE: 2

Gly Gln Gln Gln Leu Gly
1               5

<210> SEQ ID NO 3
<211> LENGTH: 11
<212> TYPE: PRT
<213> ORGANISM: Homo sapiens

<400> SEQUENCE: 3

Gly Gln Leu Lys His Leu Glu Gln Gln Glu Gly
1               5                   10
```

```
<210> SEQ ID NO 4
<211> LENGTH: 5
<212> TYPE: PRT
<213> ORGANISM: Homo sapiens

<400> SEQUENCE: 4

Phe Phe Lys Gly Cys
1               5

<210> SEQ ID NO 5
<211> LENGTH: 6
<212> TYPE: PRT
<213> ORGANISM: Homo sapiens

<400> SEQUENCE: 5

Gly Leu Gln Gln Gln Gly
1               5
```